United States Patent
Von Drasek et al.

(10) Patent No.: US 9,851,199 B2
(45) Date of Patent: *Dec. 26, 2017

(54) METHOD AND APPARATUS TO MONITOR AND CONTROL SHEET CHARACTERISTICS ON A CREPING PROCESS

(71) Applicant: NALCO COMPANY, Naperville, IL (US)

(72) Inventors: William A. Von Drasek, Oak Forest, IL (US); Sammy Lee Archer, Lynnwood, WA (US); Gary S. Furman, Jr., Saint Charles, IL (US)

(73) Assignee: ECOLAB USA INC., St. Paul, MN (US)

( * ) Notice: Subject to any disclaimer, the term of this patent is extended or adjusted under 35 U.S.C. 154(b) by 439 days.

This patent is subject to a terminal disclaimer.

(21) Appl. No.: 14/623,297

(22) Filed: Feb. 16, 2015

(65) Prior Publication Data

US 2015/0160001 A1     Jun. 11, 2015

Related U.S. Application Data

(63) Continuation of application No. 13/290,165, filed on Nov. 7, 2011, now Pat. No. 8,958,898.

(51) Int. Cl.
    *G01B 11/24*      (2006.01)
    *G06T 7/00*      (2017.01)
    (Continued)

(52) U.S. Cl.
    CPC .......... *G01B 11/24* (2013.01); *G01B 11/0608* (2013.01); *G01B 11/306* (2013.01);
    (Continued)

(58) Field of Classification Search
    CPC .... G01B 11/0608; G01B 11/24; G01B 1/306; G01N 21/86; G01N 21/8914;
    (Continued)

(56) References Cited

U.S. PATENT DOCUMENTS 3,061,944 A    11/1962   Kraus et al.
3,739,258 A *   6/1973   Karuhn ................. G01N 15/12
                                                                                      324/71.1

(Continued)

FOREIGN PATENT DOCUMENTS

JP          1996-031363      2/1996
WO       2007024858 A1    3/2007

(Continued)

OTHER PUBLICATIONS

Archer, S.,, Archer, S., Furman, G., & Von Drasek, W., "Image Analysis to Quantify Crepe Structure," Tissue World Americas 2010 Conference, Mar. 24-26, 2010, Reprint R-974.

(Continued)

*Primary Examiner* — Yuhui R Pan
(74) *Attorney, Agent, or Firm* — Eric D. Babych; Brinks Gilson & Lione

(57) ABSTRACT

The invention embodies methods and apparatuses to monitor and control the characteristics of a creping process. The method involves measuring optical properties of various points along a creped paper sheet and converting those measurements into characteristic defining data. The invention allows for determining the magnitude and distribution of crepe structures and their frequency and distribution. This allows for the generation of information that is accurate and is much more reliable than the coarse guessing that is currently used in the industry. Feeding this information to papermaking process equipment can result in increases in both quality and efficiency in papermaking.

12 Claims, 16 Drawing Sheets

(51) Int. Cl.
  *G01B 11/06* (2006.01)
  *G01B 11/30* (2006.01)
  *G01N 21/86* (2006.01)
  *G01N 21/89* (2006.01)

(52) U.S. Cl.
  CPC ......... *G01N 21/86* (2013.01); *G01N 21/8914* (2013.01); *G06T 7/0004* (2013.01); *G06T 2207/10048* (2013.01); *G06T 2207/10056* (2013.01); *G06T 2207/20056* (2013.01); *G06T 2207/30136* (2013.01); *G06T 2207/30164* (2013.01); *G06T 2207/30242* (2013.01)

(58) Field of Classification Search
  CPC . G06T 2207/10048; G06T 2207/10056; G06T 2207/20056; G06T 2207/30136; G06T 2207/30164; G06T 2207/30242; G06T 7/0004
  USPC ................................ 356/612; 700/103, 104
  See application file for complete search history.

(56) References Cited

U.S. PATENT DOCUMENTS

| | | | |
|---|---|---|---|
| 4,320,582 A | 3/1982 | Klippstein et al. | |
| 4,955,720 A * | 9/1990 | Blecha | D21G 9/0027 162/198 |
| 4,978,861 A | 12/1990 | Sabater et al. | |
| 5,123,152 A | 6/1992 | Tenkula et al. | |
| 5,179,150 A | 1/1993 | Furman et al. | |
| 5,187,219 A | 2/1993 | Furman | |
| 5,328,565 A | 7/1994 | Rasch et al. | |
| 5,571,382 A | 11/1996 | Berglund | |
| 5,654,799 A | 8/1997 | Chase et al. | |
| 5,730,839 A | 3/1998 | Wendt et al. | |
| 6,259,109 B1 | 7/2001 | Dalmia et al. | |
| 7,027,934 B2 | 4/2006 | Skeps et al. | |
| 7,408,570 B2 | 8/2008 | Gulna et al. | |
| 7,691,236 B2 | 4/2010 | Conn et al. | |
| 7,850,823 B2 | 12/2010 | Chou et al. | |
| 8,958,898 B2 * | 2/2015 | Von Drasek | G01B 11/0608 162/100 |
| 2003/0039386 A1 * | 2/2003 | Ishitani | H01J 37/222 382/141 |
| 2005/0004956 A1 | 1/2005 | Pourdeyhimi | |
| 2005/0075801 A1 | 4/2005 | Skeps et al. | |
| 2005/0244073 A1 * | 11/2005 | Keshet | G06T 5/002 382/260 |
| 2007/0204966 A1 | 9/2007 | Chou et al. | |
| 2007/0280559 A1 | 12/2007 | Ishitani et al. | |
| 2008/0023168 A1 | 1/2008 | Conn et al. | |
| 2008/0285840 A1 * | 11/2008 | Kawai | G01N 21/8851 382/141 |
| 2010/0155004 A1 * | 6/2010 | Soerens | D21H 17/35 162/111 |
| 2012/0133938 A1 * | 5/2012 | Deckers | G03F 7/70625 356/388 |

FOREIGN PATENT DOCUMENTS

| | | | |
|---|---|---|---|
| WO | WO 2007/024858 | 3/2007 | |
| WO | WO 2007024858 A9 * | 5/2007 | .......... G01B 11/306 |
| WO | 2010042606 A1 | 4/2010 | |

OTHER PUBLICATIONS

Church, E. L., Church, E. L., "The Measurement of Surface Texture and Topography by Differential Light Scattering," Wear, vol. 57 (1979), pp. 93-105.

Lidnsay, J. & Bieman, L., "Tactile Properties of Tissue with Moire Interferometry," Engineering & Papermakers: Forming Bonds for Better Papermaking Conference, TAPPI, Oct. 6, 1997.

* cited by examiner

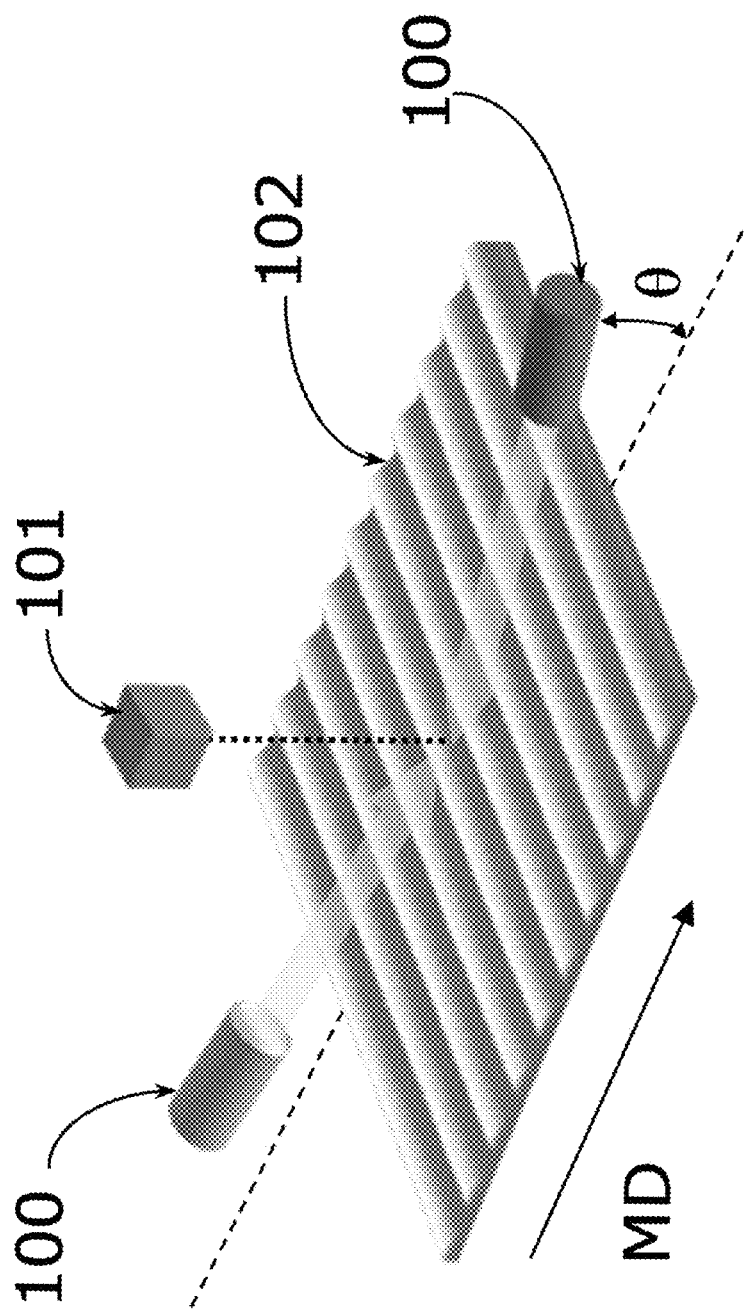

METHOD AND APPARATUS TO MONITOR AND CONTROL SHEET CHARACTERISTICS ON A CREPING PROCESS

CROSS-REFERENCE TO RELATED APPLICATIONS

This application is a continuation of, claims priority from, and incorporates by reference in its entirety co-pending U.S. patent application Ser. No. 13/290,165 which was filed on Nov. 7, 2011.

STATEMENT REGARDING FEDERALLY SPONSORED RESEARCH OR DEVELOPMENT

Not Applicable.

BACKGROUND OF THE INVENTION

This invention relates to methods, compositions, and apparatuses for the monitoring and controlling of paper sheet characteristics on a creping process. As described at least in U.S. Pat. Nos. 7,691,236, 7,850,823, 5,571,382, 5,187,219, 5,179,150, 5,123,152, 4,320,582, and 3,061,944, in the tissue manufacturing process, a paper sheet is dried and creped on a heated drying cylinder, termed a Yankee or Yankee dryer. Creping is a process in which a steel, bimetallic, or ceramic blade (called a doctor blade) is impacted into the paper sheet, thus compressing the sheet in the machine direction (MD), creating a folded sheet structure. Creping breaks a large number of fiber-to-fiber bonds in the sheet, imparting the qualities of bulk, stretch, absorbency, and softness which are characteristic of tissue. The amount of adhesion provided by the coating adhesive plays a significant role in the development of these tissue properties. Often adhesive materials are used to coat the Yankee surface in order to help the wet sheet adhere to the dryer. This improves heat transfer, allowing more efficient drying of the sheet. Most importantly, these adhesives provide the required adhesion to give good creping of the dry sheet.

The Yankee coating also serves the purpose of protecting the Yankee and creping blade surfaces from excessive wear. In this role, the coating agents provide improved runability of the tissue machine. As creping doctor blades wear, they must be replaced with new ones. The process of changing blades represents a significant source of tissue machine downtime, or lost production, as creped product cannot be produced when the blade is being changed. Release agents, typically blends of hydrocarbon oils and surfactants, are used in association with the coating polymers. These agents aid in the uniform release of the tissue web at the creping blades, and also lubricate and protect the blade from excessive wear.

In the creping process as the paper sheet is removed from the dryer surface macro and micro folds are formed that appear sharper on the air side of the sheet, while these folds are more broken up and less sharp on the Yankee side. The resulting structures formed appear as repeating bars whose MD length (machine direction) tend to be shorter than the CD (cross direction) length. Property changes to the sheet as a result of the creping process include bulk, stretch, softness, and absorbency all increasing with strength decreasing. In particular, the tactile surface smoothness of the sheet is strongly linked to the crepe structures formed on the sheet. All of these properties are critical to the manufacturer for quality control, product development, and machine troubleshooting. Controllable variables impacting the crepe structure include coating chemistry, crepe ratio (Yankee speed/reel speed), sheet moisture level, and creping blade geometry and age. Other process variables such as furnish, forming dynamics, and fabric also affect the creping process, but are not as easily controlled.

Previous methods of evaluating creped sheet characteristics and surface topography are described at least in U.S. Pat. Nos. 5,654,799 and 5,730839, US Published Patent Application 2005/0004956, International Patent Application WO 2007/024858, and Published Articles: *The Measurement of Surface Texture and Topography by Differential Light Scattering*, E. L. Church, Wear, 57 (1979), 93-105, *Tactile Properties of Tissue with Moire Interferometry*, Lidnsay, J., Bieman, L., 1997 *Engineering & Papermakers: Forming Bonds for Better Papermaking Conference*, Oct. 6, 1997, TAPPI, *Image Analysis to Quantify Crepe Structure*, Archer, S., Furman, G., and W. Von Drasek, Tissue World Americas 2010 Conference, Mar. 24-26, 2010, Miami, Fla. USA, Reprint R-974.

Monitoring the crepe structure formed in the sheet provides insight on the machine running conditions and product quality. Manufacturers recognize this point and will routinely evaluate the sample by counting macro crepe structures using an ocular device with or without image storage capability. The procedure uses an oblique light source perpendicular to the CD of the sheet, and results in scattering light from the crepe structures to visually form alternating light and dark areas. The bright areas represent crepe bars and are manually counted over a unit length scale to determine the number of crepe bars per inch (CBI) or cm. Tracking the CBI number allows the manufacturer to assess product quality and machine running conditions. For example, a reduction in the CBI number could be linked to operating conditions such as an aging doctor blade or a moisture profile change affecting the sheet adhesion. Once the problem is identified, proper corrective action can be taken to restore the desired product quality.

However, unlike tensile strength, stretch, basis weight, caliper, and moisture, which are quantitative measurements, crepe bar counting is a qualitative subjective measurement. The subjectivity in manual CBI measurements results from the complex topography of the creped sheet being composed of macro and micro structures, free fiber ends, and fractured structures. As a result, CBI analysis is dependent on the technicians experience and skill to identify and interpret what is and is not a crepe bar structure. This lack of standardization and repeatability in manual CBI measurements is a limitation in using the information for process control decisions and product quality assessment.

Thus there is clear need and utility for methods, compositions, and apparatuses for the uniform consistent and accurate measurement of creped paper sheet properties. The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 CFR §1.56(a) exists.

BRIEF SUMMARY OF THE INVENTION

At least one embodiment of the invention is directed towards a method of measuring the geometric characteristics of a crepe structure on a paper sheet. The method comprises the steps of: 1) Generating data values representing characteristics of positions on a paper sheet by repeatedly emitting at least two emission beams against each of the positions on the paper sheet and reflecting the two beams off of the positions and into a sensor constructed and arranged to absorb and measure the intensity of the reflected emission beams, 2) correcting the measured intensity of the data values by using an $n^{th}$ order polynomial fit, 3) performing a row-by-row smoothing operation of the corrected data values using a filter algorithm, 4) identifying positive to negative transitions within the smoothed data values, and 5) correlating the identified transitions with previously identified values known to correspond to particular geometric dimensions to determine geometric features of the crepe structure.

The emitted beam may be illuminating light. The sensor may be a digital camera coupled to a microscope. The emitted beam may be projected at an angle oblique to the machine direction. The emitted beam may be projected at an angle relative to the plane of the paper sheet. The emitted beam may be any form of radiation and/or any combination of radiations. The positions on the paper sheet may lie along a straight line extending in the machine direction. The filter algorithm may be one selected from the list consisting of FFT, Butterworth, Savitsky-Golay, and any combination thereof.

The method may further comprise the steps of determining the crepe frequency size distribution and converting this into a length scale. The method may further comprise the step of using more than one filtering algorithm and evaluating the results of the filtering algorithms to determine the characteristics of free fiber ends of the paper sheet. The method may further comprise the step of recognizing the periodicity of peaks in the measured data and using the periodicity to determine the softness of the creped paper sheet. The method may further comprise the step of recognizing the dispersion of peaks in the measured data and using the dispersion to determine the softness of the creped paper sheet. The method may further comprise the step of measuring both sides of the paper sheet, the method utilizing a shutter on each side of the paper sheet, the shutters constructed and arranged to block the impact of an emitted beam against a position on one side of the paper sheet when an emitted beam is impacting against the other side and also to alternate between which side is having the emitted light impact against it. The measured characteristics may be input into a system which has online control of at least some of the process equipment in a papermaking process, the system constructed and arranged to appropriately modify the settings of the process equipment if the measured characteristics are outside of a predetermined acceptable range to induce the further measured characteristics to conform to the predetermined acceptable range.

Additional features and advantages are described herein, and will be apparent from, the following Detailed Description.

DESCRIPTION OF THE DRAWINGS

FIG. 1 illustrates a perspective view of a crepe structure monitoring system.

DETAILED DESCRIPTION OF THE INVENTION

Figure 2A:
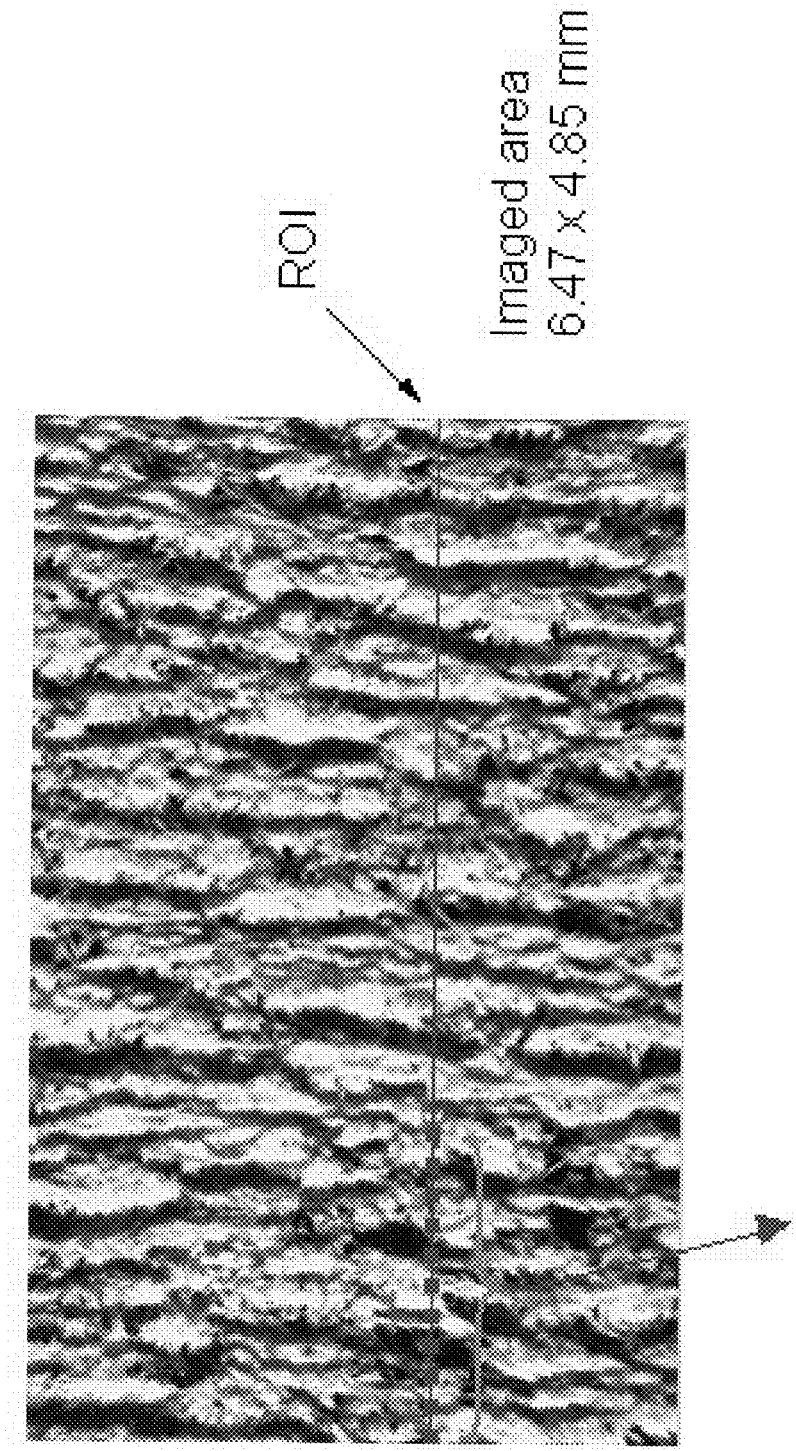
FIG. 2A illustrates a magnified view of crepe structures in one area of a tissue sheet.

The following definitions are provided to determine how terms used in this application, and in particular how the claims, are to be construed. The organization of the definitions is for convenience only and is not intended to limit any of the definitions to any particular category.

"Bevel" or "bevel surface" as used herein refers to the portion of the blade that forms the surface between the leading edge of the blade and the trailing side of the blade and is typically the "working surface" of the blade.

"Bulk" means the inverse of the density of a tissue paper web and is commonly expressed in units of $cm^3/g$. It is another important part of real and perceived performance of tissue paper webs. Enhancements in bulk generally add to the clothlike, absorbent perception. A portion of the bulk of a tissue paper web is imparted by creping.

"Crepe Structure" means the folds and seams present on a paper product that has undergone a creping process.

"Cross Machine Direction" or "CD" means the direction perpendicular to the machine direction in the same plane of the fibrous structure and/or fibrous structure product comprising the fibrous structure.

"Doctor blade" means a blade that is disposed adjacent to another piece of equipment such that the doctor blade can help remove from that piece of equipment a material that is disposed thereon. Doctor blades are commonly used in many different industries for many different purposes, such as, for example, their use to help remove material from a piece of equipment during a process. Examples of materials include, but are not limited to, tissue webs, paper webs, glue, residual buildup, pitch, and combinations thereof. Examples of equipment include, but are not limited to, drums, plates, Yankee dryers, and rolls. Doctor blades are commonly used in papermaking, nonwovens manufacture, the tobacco industry, and in printing, coating and adhesives processes. In certain instances, doctor blades are referred to by names that reflect at least one of the purposes for which the blade is being used.

"Fiber" means an elongate particulate having an apparent length greatly exceeding its apparent width. More specifically, and as used herein, fiber refers to such fibers suitable for a papermaking process.

"Highly polished" means surface that has been processed by a sequential progression from relatively rough grit to fine grit with suitable lubrication and is highly planar and substantially free of defects. Such sequential progression will be referred to herein as a "step polishing process."

"Machine Direction" or "MD" means the direction parallel to the flow of the fibrous structure through the papermaking machine and/or product manufacturing equipment.

"Oblique Angle" means an angle between 0 degrees and less than 90 degrees.

"Paper product" means any formed, fibrous structure products, traditionally, but not necessarily, comprising cellulose fibers. In one embodiment, the paper products of the present invention include tissue-towel paper products. Non-limiting examples of tissue-towel paper products include toweling, facial tissue, bath tissue, table napkins, and the like.

"Sheet control" as used herein, refers to the lack of vibrations, turbulence, edge flipping, flutter, or weaving of the web that result in a loss of control at higher speeds.

"Softness" means the tactile sensation perceived by the consumer as he/she holds a particular product, rubs it across his/her skin, or crumples it within his/her hand. This tactile sensation is provided by a combination of several physical properties. One of the most important physical properties related to softness is generally considered by those skilled in the art to be the stiffness of the paper web from which the product is made. Stiffness, in turn, is usually considered to be directly dependent on the strength of the web.

"Strength" means the ability of the product, and its constituent webs, to maintain physical integrity and to resist tearing, bursting, and shredding under use conditions.

"Tissue paper web", "paper web", "web", "paper sheet", "tissue paper", "tissue product", and "paper product" are all used interchangeably and mean sheets of paper made by a process comprising the steps of forming an aqueous papermaking furnish, depositing this furnish on a foraminous surface, such as a Fourdrinier wire, and removing a portion of the water from the furnish (e.g., by gravity or vacuum-assisted drainage), forming an embryonic web, and in conventional tissue making processes transferring the embryonic web from the forming surface to a carrier fabric or felt, and then to the Yankee dryer, or directly to the Yankee dryer from the forming surface. Alternatively in standard through air drying (TAD) tissue making processes, the embryonic web may be transferred to another fabric or surface traveling at a slower speed than the forming surface. The web is then through air dried on this fabric to a dryness typically between 50 to 90%, and finally transferred to a Yankee dryer for final drying and creping, after which it is wound upon a reel.

"Water soluble" means materials that are soluble in water to at least 3%, by weight, at 25 degrees C.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Othmer Encyclopedia of Chemical Technology,* 5th Edition, (2005), (Published by Wiley, John & Sons, Inc.) this definition shall control how the term is to be defined in the claims.

In at least one embodiment of the invention, a method determines the characteristics of a crepe structure. This method addresses the lack of standardization by using a processing methodology and apparatus to provide reliable and repeatable measurements of the sheet surface structure. In addition, the analysis provides a higher level of information compared to traditional manual CBI measurements that is helpful in developing correlations between analysis results and surface softness panel test data. Uses for the technology include quality control, product grade development, and process trouble shooting.

Referring now to FIG. 1 there is shown that in at least one embodiment the method in which a sensor device (101) and at least two emission sources (100) whose emission the sensor device is designed to detect. The emission sources (100) are oriented towards the creped structure of a paper sheet (102). Because the crepes extend roughly perpendicular to the MD the emission sources (100) emit beams at angles oblique to the CD. In at least one embodiment the emission sources (100) are also elevated above the plane of the paper sheet (102) at an angle θ. The orientation of the emission beams result in the sensor device (101) being able to resolve detailed 3 dimensional features such as crepe bars, fractured crepe bars, free fiber ends, fold depth, and fold width.

In at least one embodiment the sensor (101) is an optical sensor and/or a camera (digital or other) and the emission source (100) is a light lamp. In at least one embodiment the sensor/emission source is incandescent, LED, laser, UV, IR, and/or EM based. In at least one embodiment the sensor includes a magnification lens or is coupled to a microscope with a standardized illumination source. Image magnification is dependent on the sample, e.g., crepe bar size or frequency, and if other structural information such as embossed patterns is desired. Magnification at ~20× with a field of view in the range of 4×6 mm is a good compromise to resolve enough detail to capture crepe structures that include crepe bars, fractured crepe bars, and free fiber ends. At lower magnification, information may be lost for smaller structures such as fractured crepe bars and free fiber ends. Higher magnification is useful in analyzing these structures, but resolving the overall crepe pattern in the sheet is lost.

In at least one embodiment illumination is made by positioning the emission sources (100) on both sides of the sample perpendicular to the CD with the same angle of incidences, as shown in FIG. 1. Depending on the source characteristics, a collimating or expanding optical element may be needed to uniformly illuminate an area on the sheet larger than the camera field of view. Two sources are preferred because crepe structure identification is dependent on whether the sample is viewed from the crepe blade side or reel side. Using the combination of two illuminating sources on each side negates the manufacturing MD effect, thereby standardizing the measurement without prior knowledge on the sheet direction relative to the creping blade. For manually counting crepe bars, a dual light illumination method is not critical, since macro crepe bar structure lengths are not measured but rather counted over a known length scale.

The topography of a creped sheet is a complex 3-dimensional structure composed of macro and micro folds, fractured crepe structures, and free fiber ends. In addition, these structures can vary in height and spacing between one another. As a result, detecting the scattered light from the top of these structures using a shallow angle illumination source is dependent on the direction that the light is propagating. The directional dependency results from light getting blocked by neighboring structures, thereby producing a darker region in the image. Processing the image from the ROI (region of interest) intensity profile to identify a crepe structure will display a shift in the profile toward the direction of the illumination source. To illustrate this point, FIG. 1 shows a ROI intensity profile over a 2.0 mm distance collected with light sources independently illuminating the right and left sides of the sample, as well as with both light sources illuminating the sample simultaneously. With right side illumination only the profile shifts to the right because the scattered light intensity is dominant on the right side of the crepe structures. In this case, light scattering from nearby structures on the left side is attenuated or lost. Similarly, illuminating the sample only from the left side exhibits the same characteristics. Illuminating the sample simultaneously from both the left and right side captures the surface structures from both directions resulting in more detail.

Referring now to FIG. 2A there is shown an image collected using the invention. The two or more sources produce features undulating between light and dark which represent the detailed characteristics of the crepe structure. One of ordinary skill in the art would understand that the light and dark regions are merely indicators of different characteristics and any other means of noting two or more different characteristics is encompassed by this invention. The brighter regions correspond to structural features with high amplitude, e.g., the peak of a fold, on the sheet that scatter emissions from the illumination source whereas dark regions represent regions where emission penetration is poor. This variation in intensity can be used to identify and measure crepe structures on the sheet surface.

Figure 2B:
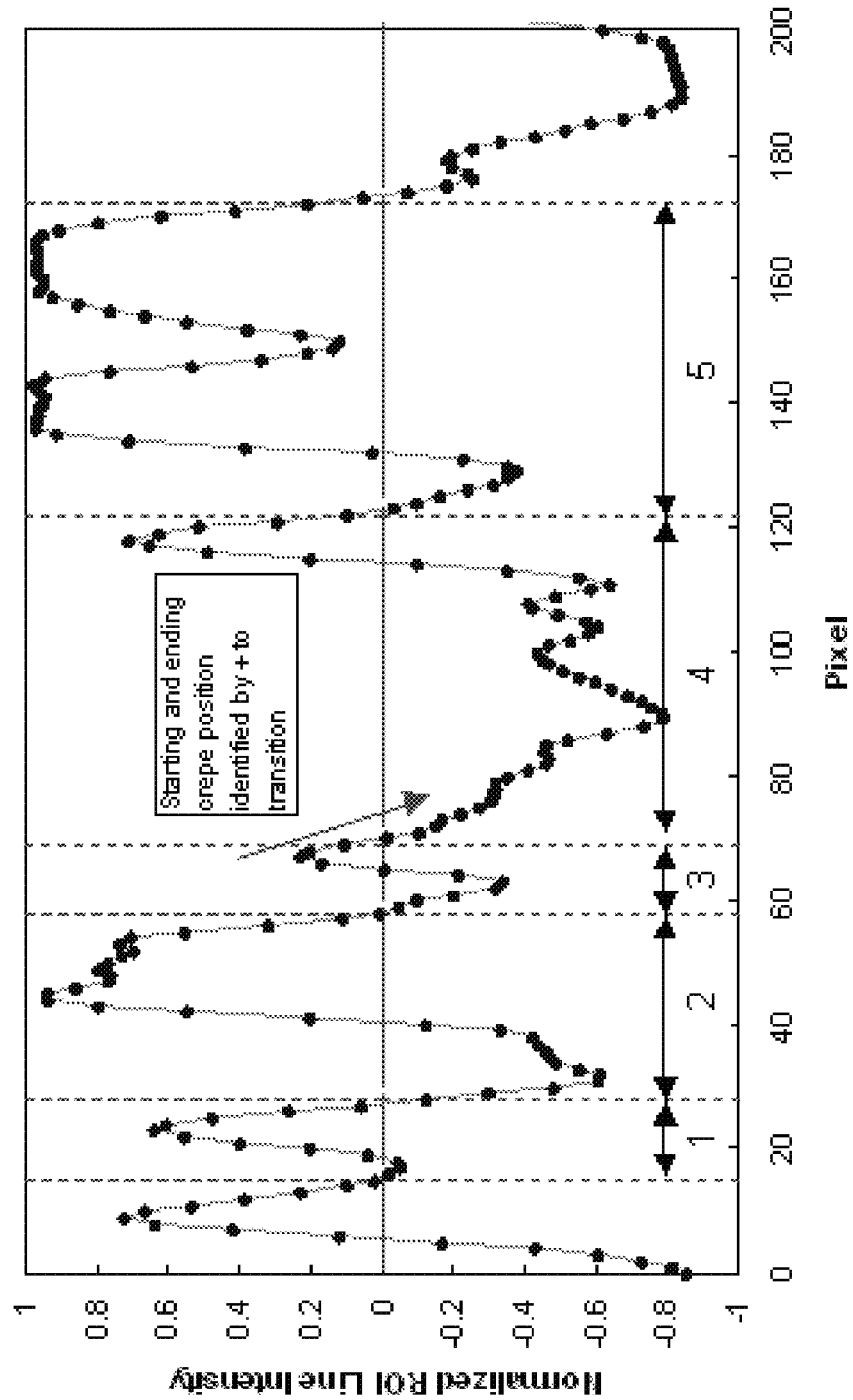
FIG. 2B is a graph of light intensity vs. pixel for a chosen ROI of a crepe structure.

To illustrate the processing steps performed FIG. 2A shows a tissue paper image captured with a digital 8-bit camera using a 20× magnification lens system. At this magnification, the full image is approximately 6.4 mm wide (1024 pixels) by 4.85 mm high (768 pixels). The horizontal line on the image represents the ROI (region of interest) used to measure the variation in light intensity along the line with gray scale values ranging between 0 (black) to 255 (white). Variation in the light intensity along the ROI line is shown in FIG. 2B for the first 200 pixels. For manual counting of the crepe features, the high intensity values along the ROI are counted over a known length scale. The crepe frequency is then the total number of features counted divided by the length scale. The method developed here automates the procedure by identifying crepe features on each row of pixels over the entire image. This approach not only standardizes the means to identify crepe features that can be used to determine a crepe frequency (CBI) comparable to manual counting, but also gives information on the feature size distribution statistics.

In at least one embodiment automation of crepe feature identification uses the following steps:
1. Row-by-row baseline correction using an $n^{th}$ order polynomial fit (generally a $2^{nd}$ or $3^{rd}$ order polynomial is adequate to remove baseline curvature) to correct intensity variation of the image. The degree of baseline correction will depend on the magnification and uniformity of the illumination source incident on the sample. The baseline correction is made by taking the point-by-point difference between the ROI intensity profile and the polynomial fit. As a result, the mean of the corrected profile approaches zero,
2. Perform a row-by-row smoothing operation using a filter algorithm, e.g., FFT, Butterworth, Savitsky-Golay, etc., to reduce high frequency variations in the profile caused by noise and/or small features. Filter parameter selection is critical to distinguish between macro and micro structures. In manual crepe counting only macro structures are used. Inclusion of micro structures in the analysis will result in crepe frequency counts higher than typical manual counting. This does not mean that micro counts are not useful; it only means that filtering is needed to get results comparable with manual counting that tissue makers are familiar with, and
3. Crepe feature identification is made by tracking (left to right) along the ROI line to identify positive to negative intensity transitions. Identified adjacent transitions represent the beginning and ending point of a crepe feature. The identification points are shown by vertical markers on FIG. 2B for the first five crepe features identified along the 200 pixel ROI line and the number of pixels between the markers represents the feature size. By calibrating the imaging device with an object of known dimensions, the number of pixels defining the feature is converted to a length scale.

Steps 1-3 can be automated to perform a row-by-row analysis over the entire image to collect the number and size of each crepe structure identified. The processed results can then be displayed as a frequency (or percent frequency) size distribution plot in addition to a quantitative summary of the data set using standard descriptive statistics. Further reduction in the data can provide metrics that mill operators are accustomed to working with. For example, mills typically use crepe bars per inch (CBI) as a metric to assess operating conditions and product quality. A CBI metric from the processed image data is obtained by taking the reciprocal of the mean feature size from the distribution plot. To utilize the size distribution data more efficiently a breakdown in the distribution plot can be made by categorizing the feature size as fine, medium, coarse, and very coarse. This breakdown allows the operator to make a quick evaluation of the product quality to determine if any process changes are needed or not.

In at least one embodiment a method is used to transform the crepe frequency size distribution to a length scale or % length scale. This transformation effectively places more weight on the larger structures, thus providing a more sensitive indicator to the tactile feel of the sheet surface. For example, a higher density of large structures (structures>0.5 mm) indicates a coarser sheet compared to a sample with a lower density of large structures. Transformation to length scale is made in two steps. First, the total length of the image is determined by summing the features identified for all rows. Second, a subset of summed lengths is made for a predetermined range, e.g., the sum of features in the size range between 0.1 and 0.15 mm. The percentage is determined by dividing the summed subset of lengths by the total length. The procedure is repeated for different size ranges to form a % length scale plot as a function of the feature size. Similar to the frequency distribution, the length scales can be categorized as fine, medium, coarse, and very coarse to provide an efficient means to observe shifts between different length scale sizes and aid in process adjustment decisions.

In at least one embodiment the method compares and correlates the fine structures, e.g., free fiber ends or micro structures, on the sheet surface by evaluating the row-by-row profile data processed in steps 1-3 discussed above at different filtering conditions. For example, data filtering using the Savitsky-Golay method for a $1^{st}$ order polynomial with side points varying from 5 to 50 is used to generate a set of feature size distributions. The mean value from each distribution at a specific filter condition is then used to calculate a set of values defined as crepe structures per inch (CSI). Here the CSI value is determined using the same method as CBI. The difference being that CSI can include both macro and micro structures where CBI is specific to macro structures. Plotting the CSI values as a function of filter points produces a decay curve as in FIGS. 3A-3C for a set of three different samples with varying softness. Characteristic features of the curve shows an exponential decay starting at high CSI values for low filter (micro plus macro structures) conditions that approaches an asymptotic limit as filtering is increased (macro structures). Samples with a high density of surface structures, e.g., free fiber ends and fractured crepe structures, will exhibit a high sensitivity to changes in the filter level. Conversely samples with a low density of surface structures show less sensitivity to changes in the filter parameters. The characteristics of the curves in FIGS. 3A-3C such as maximum CSI, delta between maximum CSI and asymptotic limit, slope, etc., provide useful metrics in developing correlations with surface softness from consumer or expert panel tests. Further refinement in developing correlations with softness is possible using a combination of these characteristics with the descriptive statistics from size distribution data as well as size breakdown results.

Figure 3A:
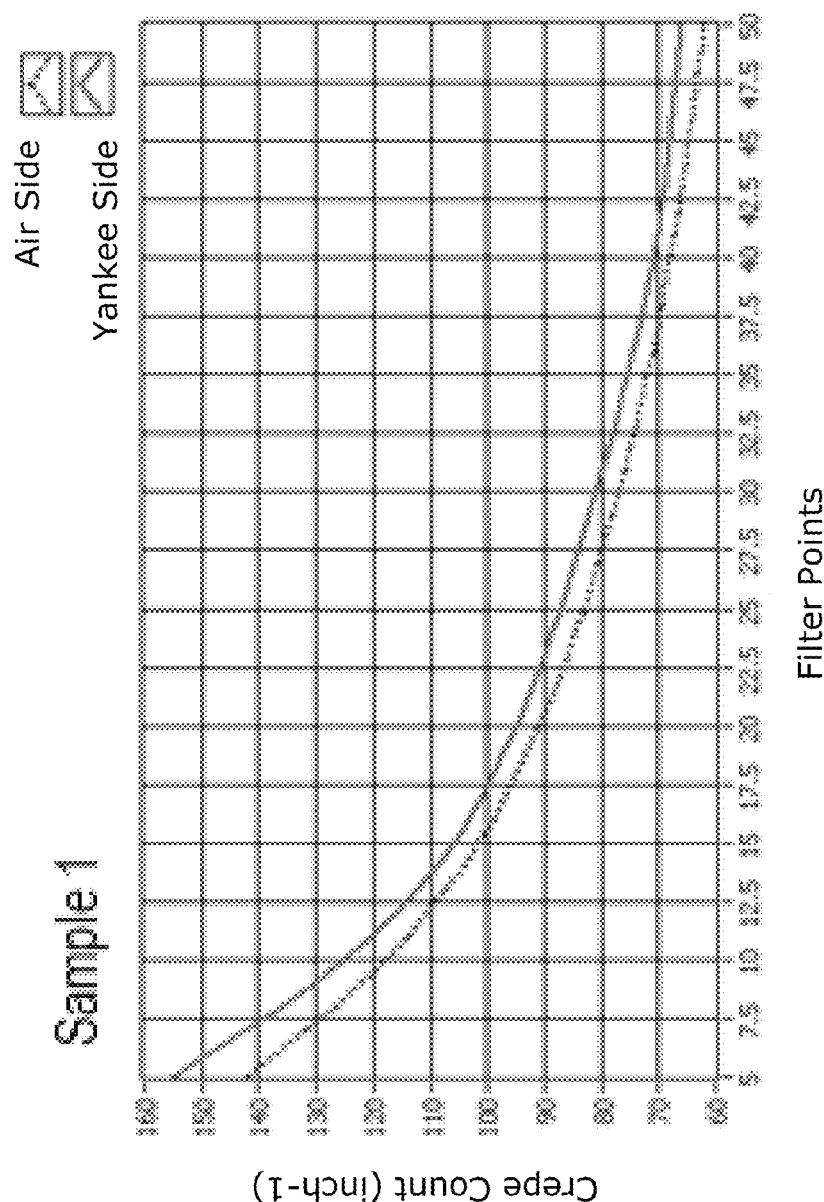
FIG. 3A is a first graph of CSI decay curves of a tissue sample.
Figure 3B:
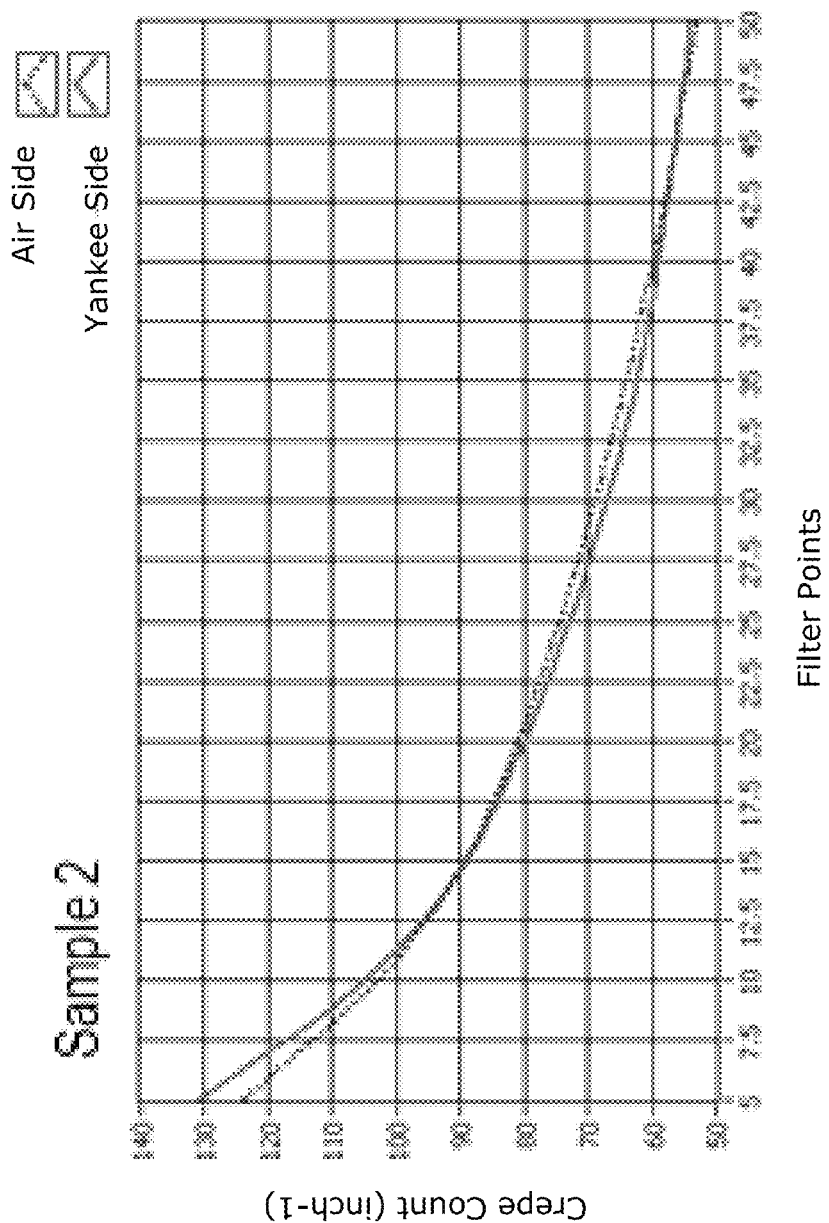
FIG. 3B is a second graph of CSI decay curves of a second tissue sample.
Figure 3C:
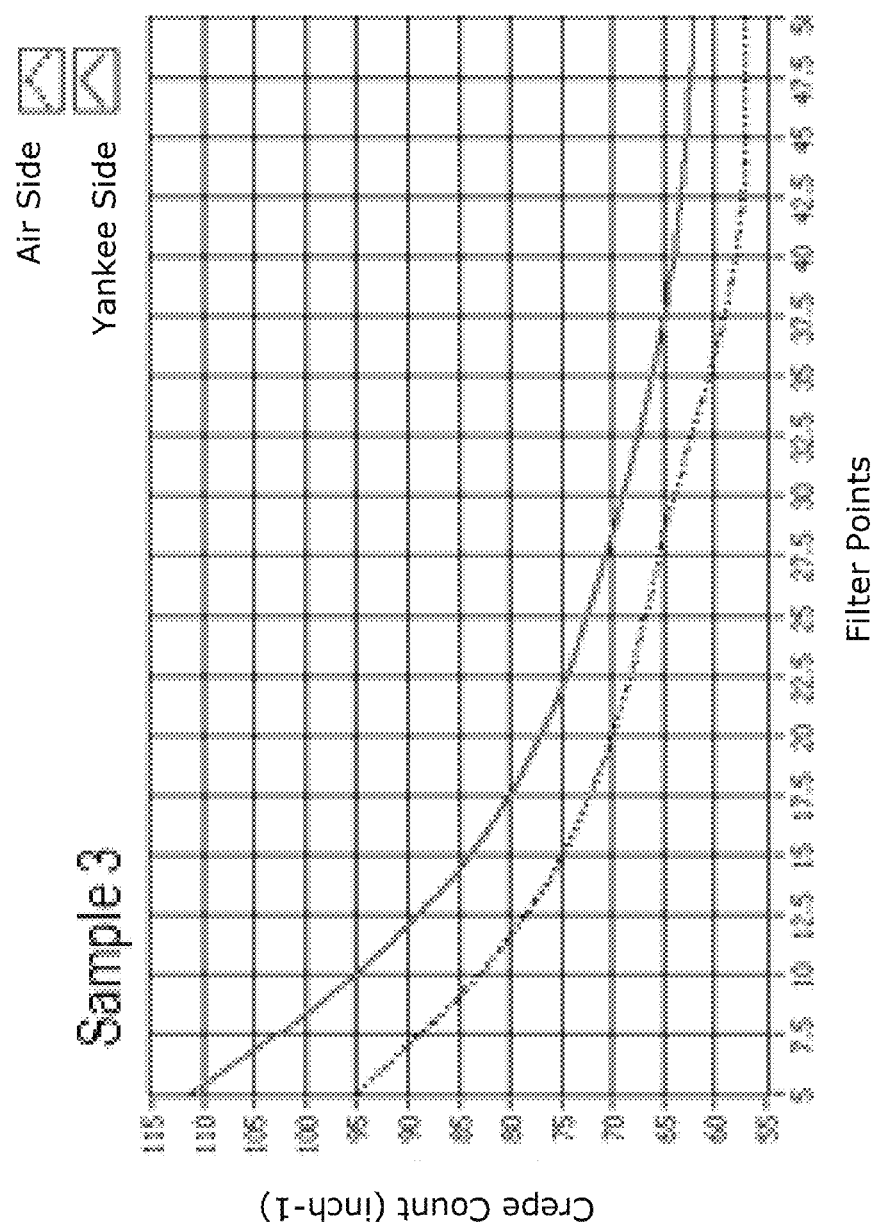
FIG. 3C is a third graph of CSI decay curves of a third tissue sample.
Figure 4A:
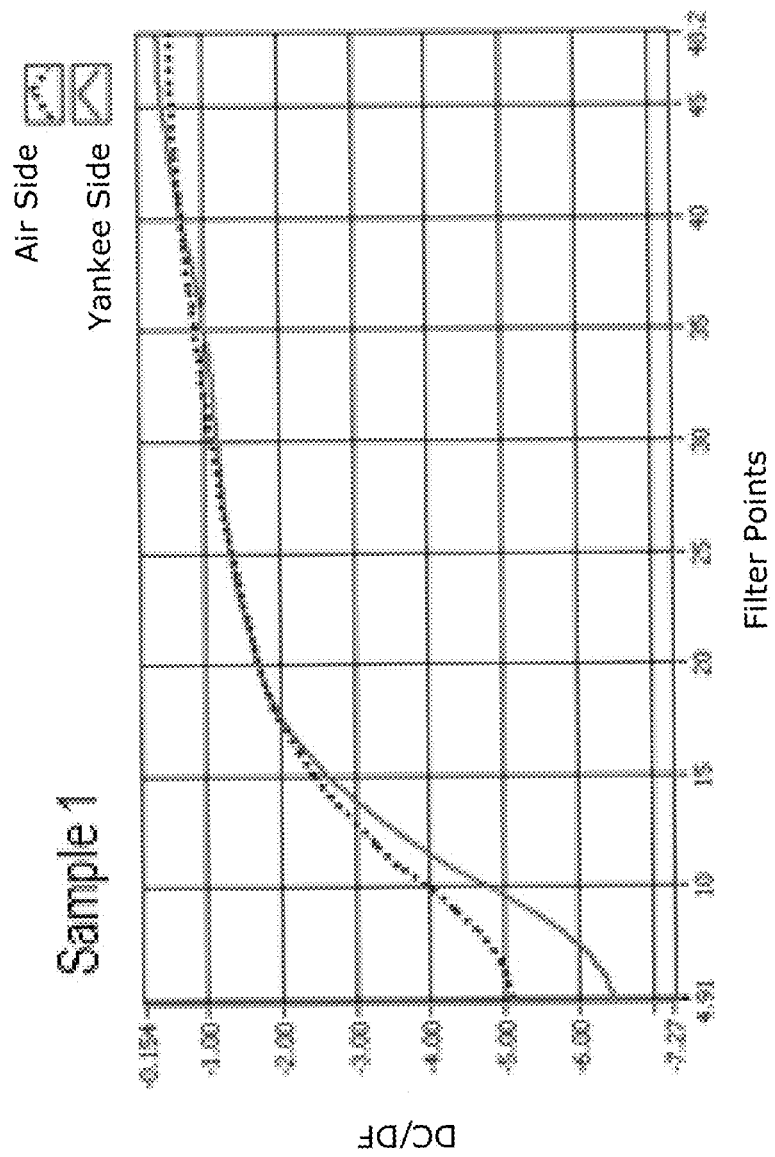
FIG. 4A is a first graph of marginal CSI values determined from FIG. 3A.
Figure 4B:
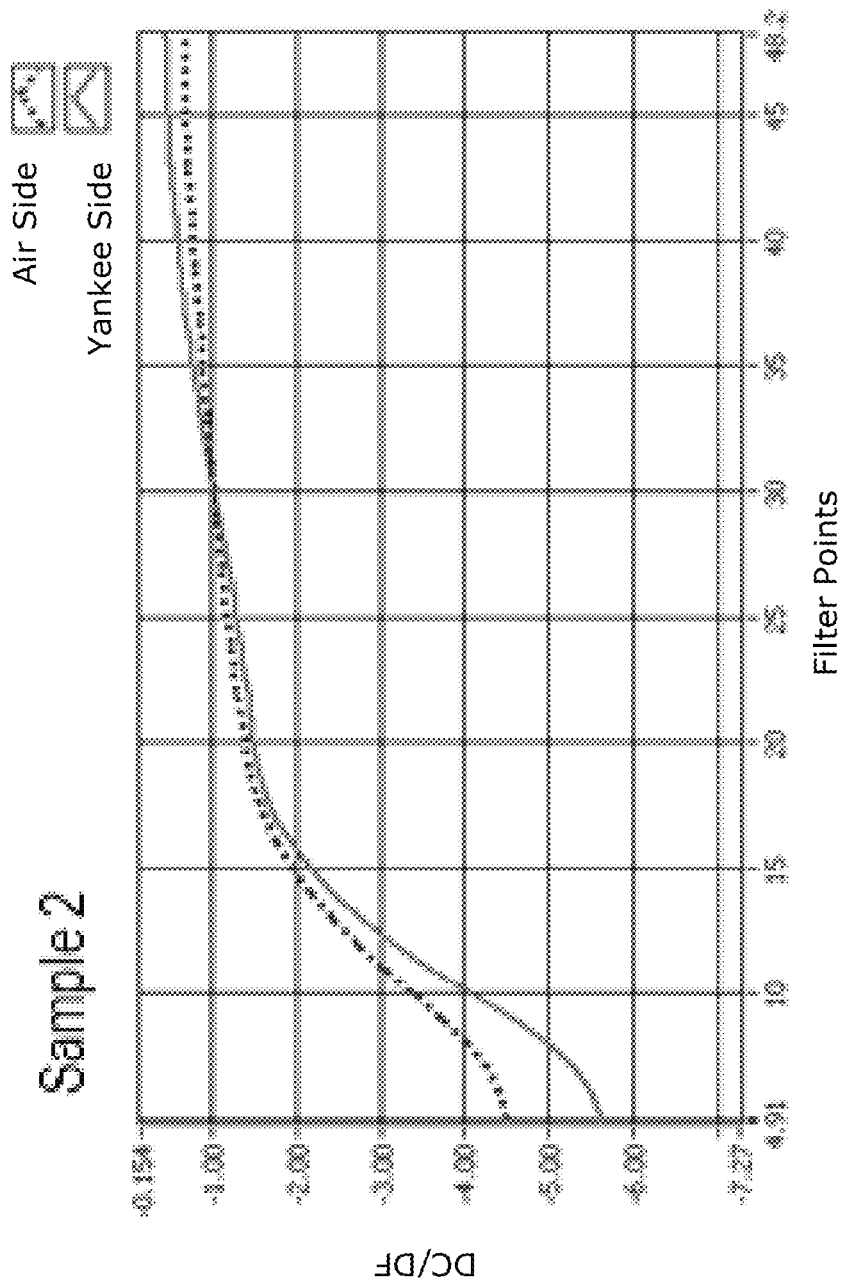
FIG. 4B is a second graph of marginal CSI values determined from FIG. 3B.
Figure 4C:
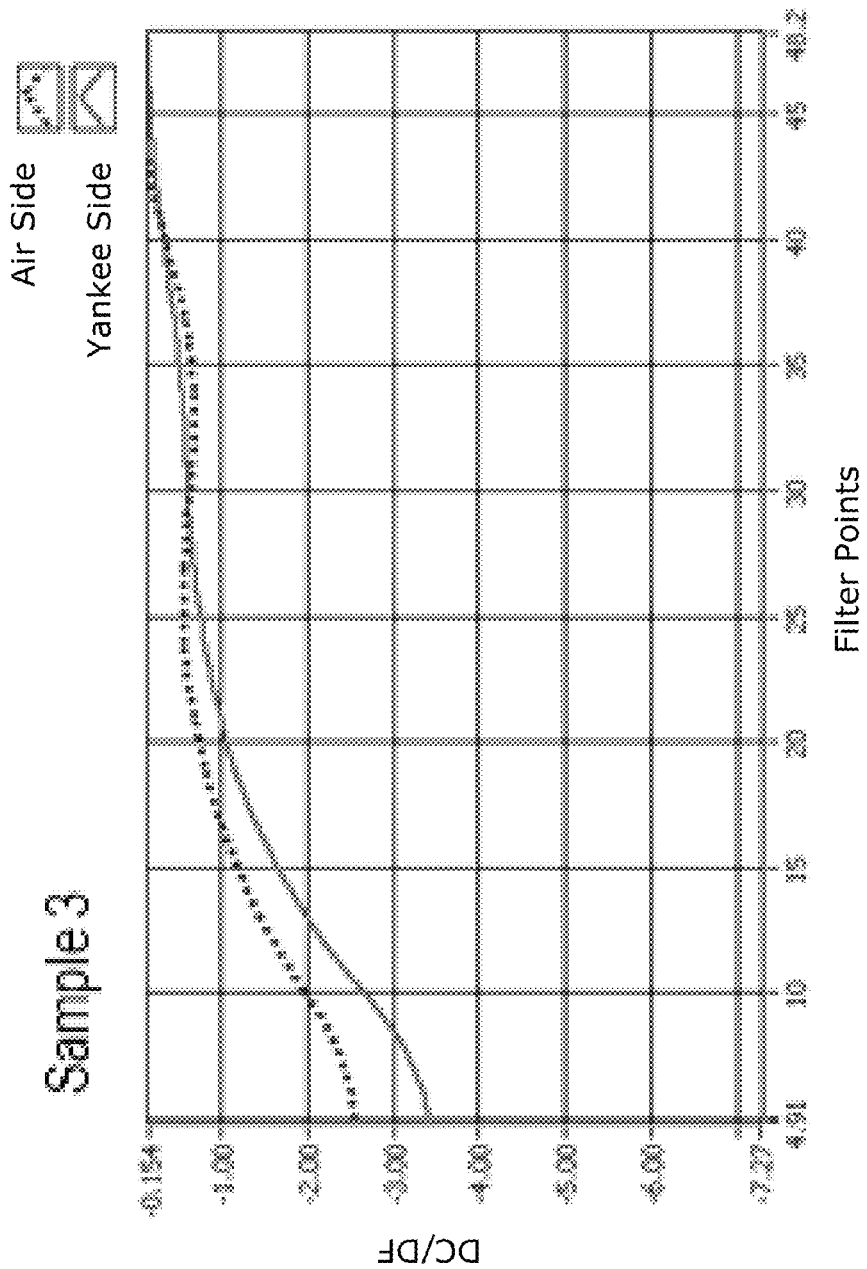
FIG. 4C is a third graph of marginal CSI values determined from FIG. 3C.
Figure 5:
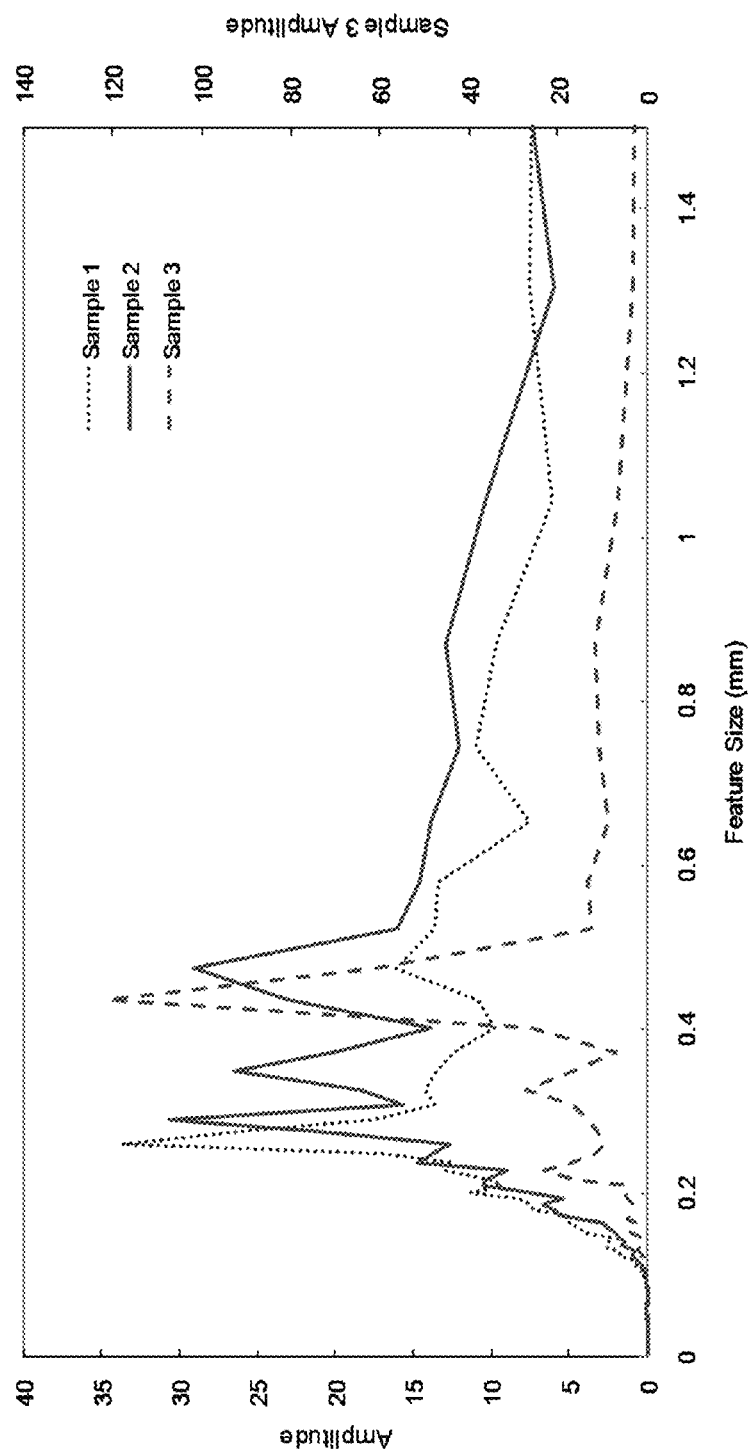
FIG. 5 is a graph of cumulative FFT spectra for three tissue samples.

Taking the first $1^{st}$ derivative of the decay curves shown in FIGS. 3A-3C gives the marginal CSI curves shown in FIGS. 4A-4C. Marginal CBI represents the change in the CSI value for a change in the number of points used with the Savitsky-Golay filter. Information extracted from the filter analysis, summarized in Table 1, compares the standard CSI values from the feature size distribution, the delta CSI values from the raw filter data, and the slopes from the marginal CBI plot. The samples listed are ranked from 1 to 3 based on tactile feel with 1 having the best surface softness and 3 being the worst. The additional information from the filter analysis extends the level of interpretation. For example, a large ΔCSI value is an indicator of the small feature population. Comparing differences between the standard CBI and ΔCSI values for air and Yankee sides shows the delta analysis gives a larger value. The difference is even greater for the marginal slope analysis when comparing the percent change value (percent change represents the increase in the value (CBI, ΔCSI, and Marginal slope) between air to Yankee sides) for each analysis. Therefore, the varying filter analysis provides a higher sensitivity to surface changes.

the periodic features emerge as unique peaks in the spectrum. Peak amplitude is an indication of the sample periodicity while dispersion of the peak or baseline indicates the randomness in the structures. FIG. 5 compares cumulative FFT analysis results for the three tissue samples with varying degrees of softness previously referred to in Table 1. Sample 1 is ranked as having the best surface softness, and shows a unique peak at 0.26 mm that resides on a broad baseline. Comparatively sample 2, which is ranked as having poorer softness, shows multiple peaks at larger feature sizes. The peak amplitudes and baseline level for the two samples are comparable, but the additional peaks that appear in sample 2 contribute to a reduction in softness. The lowest ranked sample 3 shows a strong peak at 0.435 mm indicating a highly periodic structure in the sheet. The combination of high periodicity and large structure size results in sample 3 having the poorest surface softness.

Another important feature from the cumulative FFT analysis is the peak dispersion. Higher dispersion in the peak indicates the distribution of structures identified is spread over a larger range. For sample 2, the peak at 0.474 mm is broad indicating the distribution of structure sizes span a large range of values. To reduce the cumulative FFT spectrum to a useful metric that influences surface softness, the integrated peak dispersion PD given by $$PD = P_A \int_{x_o}^{x_t} A(x) dx$$

where $P_A$ is the peak amplitude and $A(x)$ is the amplitude as a function of the feature size can be used. For example, the PD value for the first and third peaks of sample 2 is 0.16 and 0.41 respectively indicating the third peak has a stronger negative influence on surface softness because the value is larger. The calculated PD values from the cumulative FFT spectrum of a sample can be combined with other processing methods described here to develop softness correlations.

Figure 6:
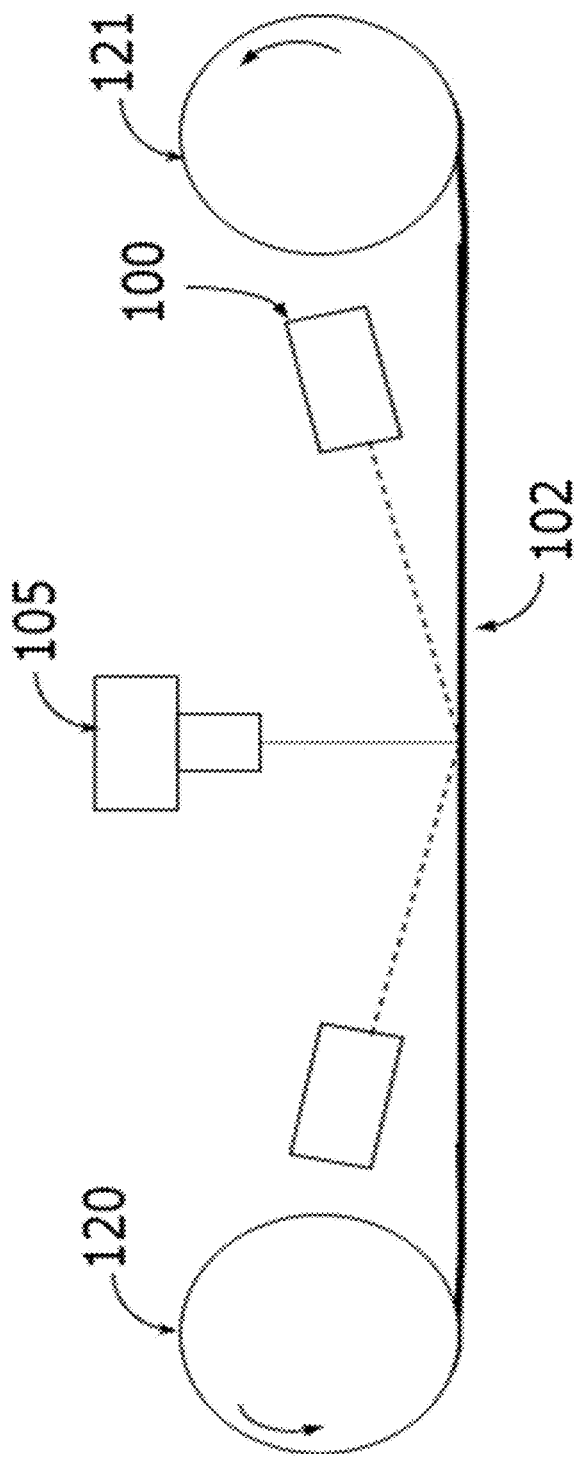
FIG. 6 is a side view illustration of a device for evaluating CD profiles of crepe structures in tissue sheets.

In at least one embodiment the method involves combining the different analysis methods with an automated off-line instrument to analyze crepe structures at multiple CD locations. The apparatus shown in FIG. 6 comprises an illuminating source (100) and sensor (105). The sheet sample is moved across the imaging plane by spools (120) and (121). A sample strip of varying length up to and including the full CD is placed on a spool (120). Because of geometric constraints a lead affixed to both ends of the sample and to the reels (120 and/or 121) can be used to allow image capturing at the edges. Image collection is made either asynchronous or synchronized to the reel position. In the synchronous mode, images are captured at known CD positions as the sample is translated across the imaging plane. Processing is performed to construct a CD profile for different metrics, e.g., CBI, CSI, marginal slope, % fine, etc.,

TABLE 1

Filter analysis results from samples with different softness ranking (1 = best, 3 = worst).

| Sample | Softness Ranking | CBI std. Air | CBI std. Yankee | % Change | Δ CSI Air Side | Δ CSI Yankee Side | % Change | Marginal Air Slope | Marginal Yankee Slope | % Change |
|---|---|---|---|---|---|---|---|---|---|---|
| 1 | 1 | 103 | 106 | 2.83 | 80 | 89 | 11.25 | 0.328 | 0.469 | 30.06 |
| 2 | 2 | 90 | 91 | 1.10 | 71 | 78 | 9.86 | 0.314 | 0.426 | 26.29 |
| 3 | 3 | 75 | 85 | 11.76 | 38 | 49 | 28.95 | 0.171 | 0.217 | 21.20 |

In at least one embodiment the method uses a cumulative FFT analysis of at least one of the corrected profiles processed following steps 1-3 described above. By summing the frequency spectra from each row the cumulative effect of using the various analysis methods described here. For example, a CD analysis of CBI values coupled with moisture profile data is a useful check of how CBI variations correlate with moisture.

Figure 7:
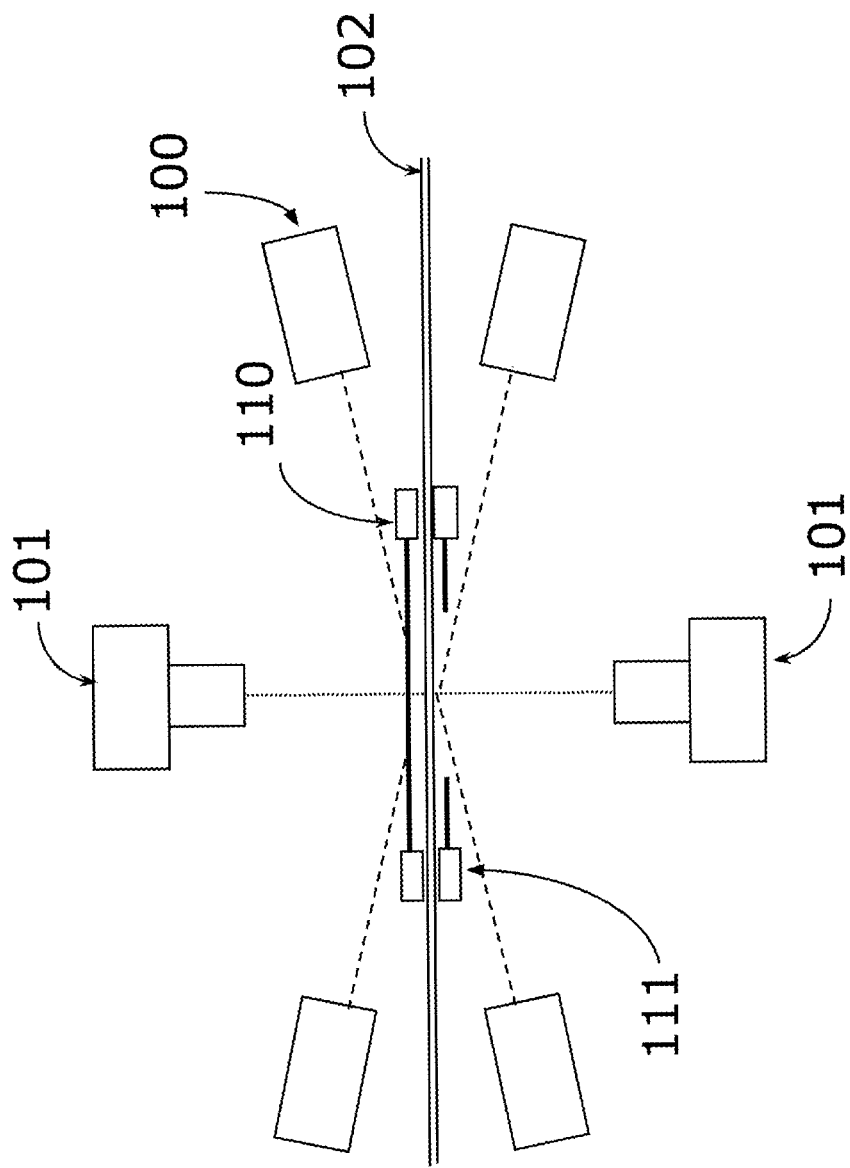
FIG. 7 is a side view illustration of a system for spatially synchronized two sided monitoring of crepe structures in tissue sheets.

In at least one embodiment more than one mode of analysis is performed. For example a dual monitoring system for near simultaneous imaging of both sides of the sheet at the same location is used to monitor sheet two-sidedness. The apparatus shown in FIG. 7 consists of a multiple sensors (101) and illumination sources (100). The paper sheet (102) can be stationary or moving either continuously or at discrete increments. To prevent interference of emission beams a sheet shutter (110) is used to isolate each side from the light source to provide a dark background for improved contrast. In this mode of operation, the shutter (110) is closed on one side while the shutter on the opposite side is opened to collect the image. The procedure is then reversed to collect an image on the opposite side. Imaging made at the same location for both sides of the sheet is useful for two sidedness analysis, i.e., the difference in crepe structures between the air side and Yankee side. Higher adhesion will result in more surface structures on the Yankee side producing a softer surface.

Figure 8:
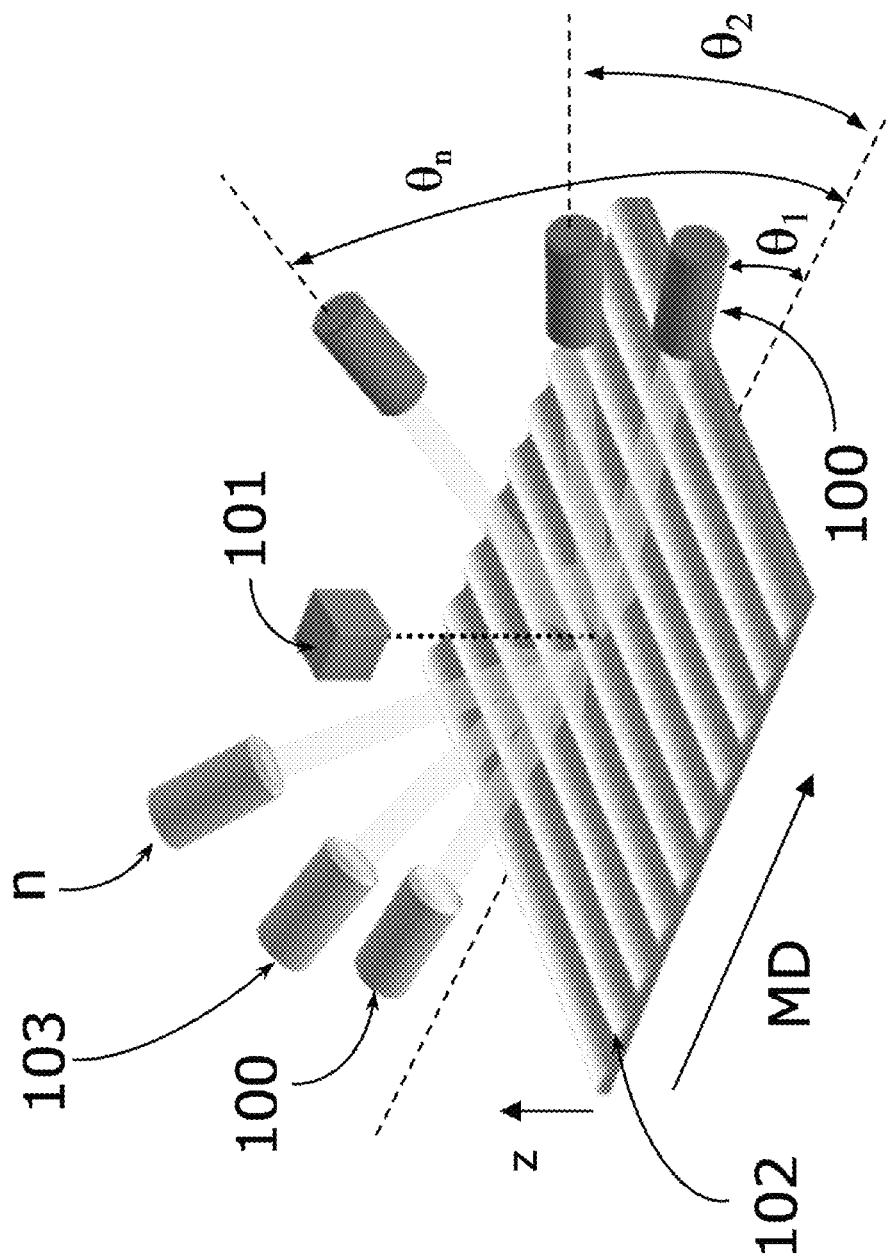
FIG. 8 is a perspective view of a system using multiple illumination sources.

In at least one embodiment there is an apparatus that combines multiple emission sources symmetric about the sensor normal positioned at various angles, as shown in FIG. 8. The illuminating source can be fixed or translated to different angles. In FIG. 8 a set of emission sources (100) and (103) are positioned at angles $\theta_1$ and $\theta_2$ respectively. Image acquisition is made with sample emission using only one set of sources at a time. Up to n illuminating sources can be used to generate n images acquired for each set of sources. At oblique angles, e.g., $\theta_1$, the contrast between the high amplitude structures and low areas is enhanced resulting in clearly defined modulations indicated by the dark and light intensity regions in the image. Increasing the source angle $\theta$ will allow the light to penetrate areas between the high amplitude structures, thus decreasing the contrast between high and low structures. The change in light intensity measured as a function of the illuminating source angle can then be related to the surface structure height.

This relationship can be determined by either calibrating the system or from light scatter theory. Another application using multiple illuminating light sources is to remove embedded structures in the sheet. In this case, the images are collected with set of illuminating sources near normal to the sample and the other set at an oblique angle. The image captured with the near normal illuminating source is analyzed by FFT to remove embedded structures in the sheet that occurs from the fabric during the forming process. Embedded structures from the fabric are periodic and can be analyzed using the any of the processing methods described here for crepe structure analysis. Analysis results of the embedded structure sample can be compared with analysis results from the creped sheet image captured using the oblique illuminating source. Differences between the embedded and creped sheet analysis results are useful information for tissue makers to benchmark their process. This helps them understand if they are limited by the fabric or not to increase the crepe count in the sheet for improved softness.

In at least one embodiment there is a system configured for capturing images on-line with one or a combination of the processing methods described here. In this mode of operation real-time or near real-time analysis of the crepe structure is collected to assess product quality. Adapting any of the system configurations described here for on-line monitoring is complicated by processing speed (3000-7000 fpm) and sheet flutter (vertical movement of the sheet). Though technically challenging both of these issues can be addressed with high speed cameras and illumination sources as well as sheet stabilizing techniques. Additional complications arise for CD scanning in the translation hardware and data collection.

EXAMPLES

The foregoing may be better understood by reference to the following example, which is presented for purposes of illustration and is not intended to limit the scope of the invention.

Figure 9:
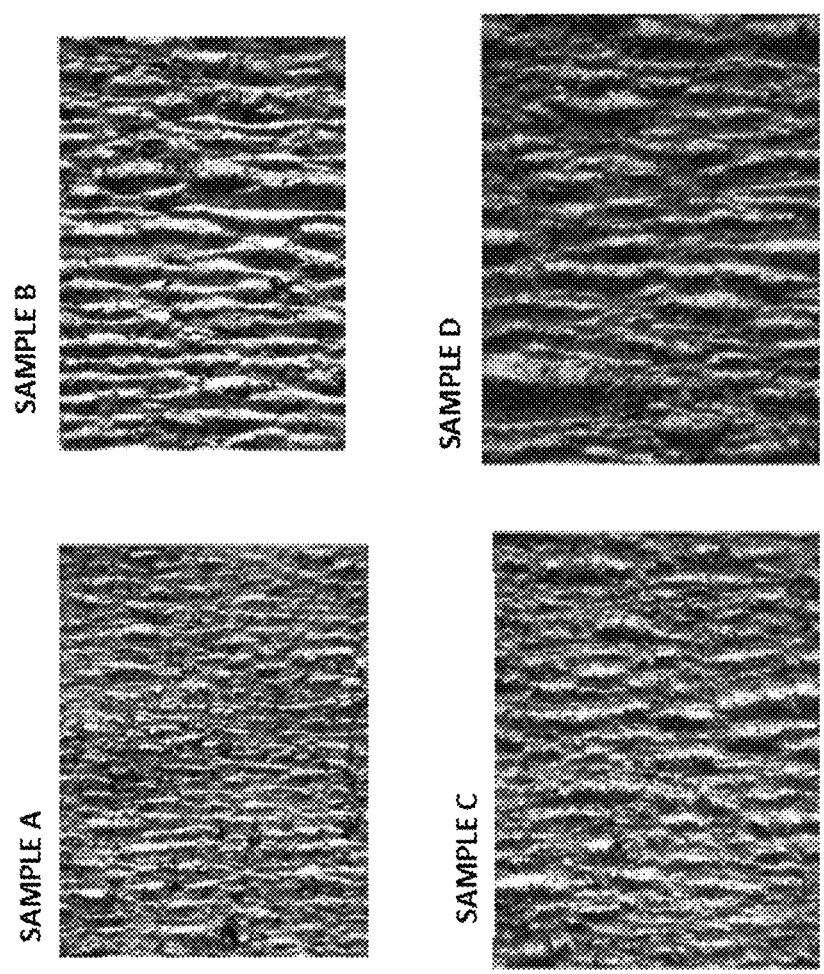
FIG. 9 is a set of four different tissue sample images labeled A,B, C, and D used in the comparative analysis of Example 1.

The standardized processing methodology and apparatus of this invention were used to characterize the four tissue images shown in FIG. 9. These images were acquired at 20× magnification. To highlight the improvement provided by this invention compared to past practices, the images were also provided to ten experienced tissue technologists skilled in the art of manual crepe counting. A calibrated length scale was provided with the images to aid in the manual analysis. The results of the manual analysis are provided in Table 2, and compared to the results from the standardized processing using the current invention in Table 3.

TABLE 2

Manual crepe analysis results from ten trained technologists of the tissue images provided in FIG. 9. All values provided in units of crepes/inch.

| Sample | Individual Measurements | Average | Standard Deviation |
|---|---|---|---|
| A | 100, 130, 120, 100, 80, 70, 100, 90, 110, 80 | 98.0 | 18.7 |
| B | 80, 100, 100, 80, 80, 70, 90, 80, 90, 70 | 84.0 | 10.7 |
| C | 70, 90, 90, 70, 70, 50, 70, 70, 80, 60 | 72.0 | 12.3 |
| D | 60, 80, 90, 70, 70, 60, 60, 80, 90, 70 | 73.0 | 11.6 |

TABLE 3

Crepe analysis by the method and apparatus of this invention for the tissue images provided in FIG. 9.

| Crepe Statistics | Sample A | Sample B | Sample C | Sample D |
|---|---|---|---|---|
| Avg. Crepe Count (crepes/cm) | 102.2 | 80.6 | 85.5 | 75.9 |
| Mean (mm) | 0.249 | 0.315 | 0.297 | 0.334 |
| Std. Deviation (mm) | 0.113 | 0.138 | 0.136 | 0.170 |
| Median (mm) | 0.234 | 0.297 | 0.285 | 0.304 |
| Mode (mm) | 0.195 | 0.197 | 0.204 | 0.216 |
| Skewness | 1.145 | 0.695 | 0.668 | 1.096 |
| Kurtosis | 5.877 | 3.458 | 3.667 | 4.872 |
| % Fine | 56.26 | 36.36 | 41.52 | 36.85 |
| % Medium | 35.89 | 49.16 | 47.30 | 44.93 |
| % Coarse | 2.47 | 9.02 | 6.42 | 11.39 |
| % Very Coarse | 5.38 | 5.46 | 4.76 | 6.83 |

The average crepe counts per inch (CBI) show relatively good agreement between the manual analysis and the automated analysis of this invention. However as shown by the large spread in individual measurements, there was a large amount of subjectivity in the manual analysis between technicians. Since this data was averaged from ten individuals, the average is more representative of the actual crepe frequency in the images. In practice, only one technician will be present to analyze a sample and the problem of subjectivity in manual analysis becomes clear.

On the other hand, the average crepe count in Table 3 is the average of 768 individual line scans and is a much more representative and objective value. In addition the method and apparatus of this invention provides a much greater level of detail regarding the crepe structures in the tissue sheet than is possible from the manual analysis of past practice. New information includes the mean width of the crepe structures and descriptive statistics of the frequency distribution of the crepe width sizes. Finally the distribution plot is categorized in terms of fine, medium, coarse and very coarse crepe structures.

Applying cumulative FFT and marginal CSI analysis to the set of images in FIG. 9 provides additional information on the surface structure periodicity, surface variations such as free fiber ends, fractured crepe structures, and MD crepe length, and structure density. Using this information in combination with standard crepe frequency, i.e., CBI, helps in developing tactile surface feel correlations, empirical categorization, and benchmark analysis.

Figure 10:
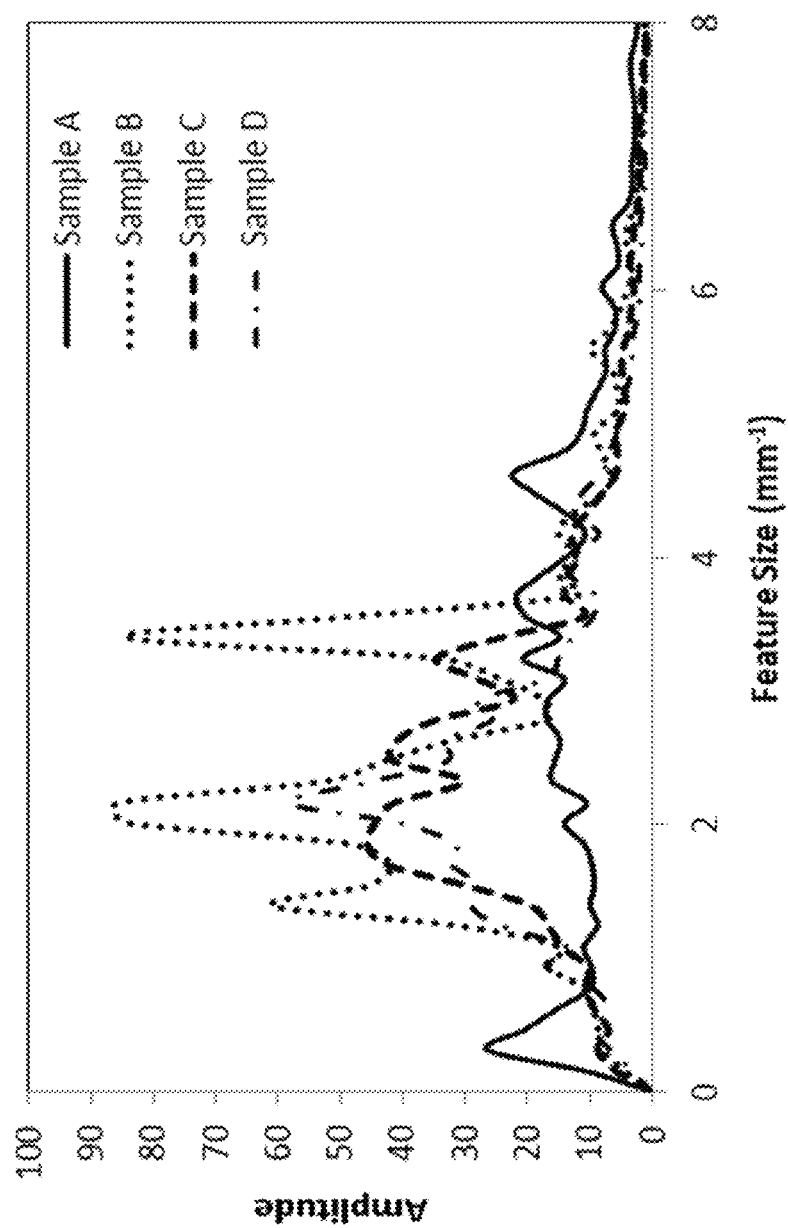
FIG. 10 is a graph of cumulative FFT spectra for images in FIG. 9.

The cumulative FFT analysis result shown in FIG. 10 gives insight into the surface structure periodicity. For example, a cumulative FFT analysis of a sample with high periodicity results in a spectrum with distinct peaks at the dominate feature size. This characteristic is seen in the cumulative FFT spectrum for sample B in FIG. 10, which shows three distinct peaks at 3.4, 2.0, and 1.4 $mm^{-1}$ that reside on top of a broad baseline structure. In contrast, sample A shows a lower periodicity with only a few low amplitude peaks at 0.31, 3.24, 3.71, and 4.63 $mm^{-1}$ on the broad baseline structure. If little or no periodicity is maintained in the CD as the analysis marches along the MD, then no distinct peak will appear. In this case, the cumulative FFT spectrum would appear only as a broad baseline structure because periodic CD features will not constructively build to form a peak. Samples with high periodicity have crepe structures that are well defined in the MD with length scales greater than low periodicity samples. The combination of periodic structures with long MD length scales contributes to the high amplitude well defined peaks in the cumulative FFT spectrum, as shown in FIG. 10 for sample B. Surfaces with these characteristic features will have a coarser tactile feel because the density of structures in contact with one's finger is less compared to a sample with randomly distributed structures.

Figure 11:
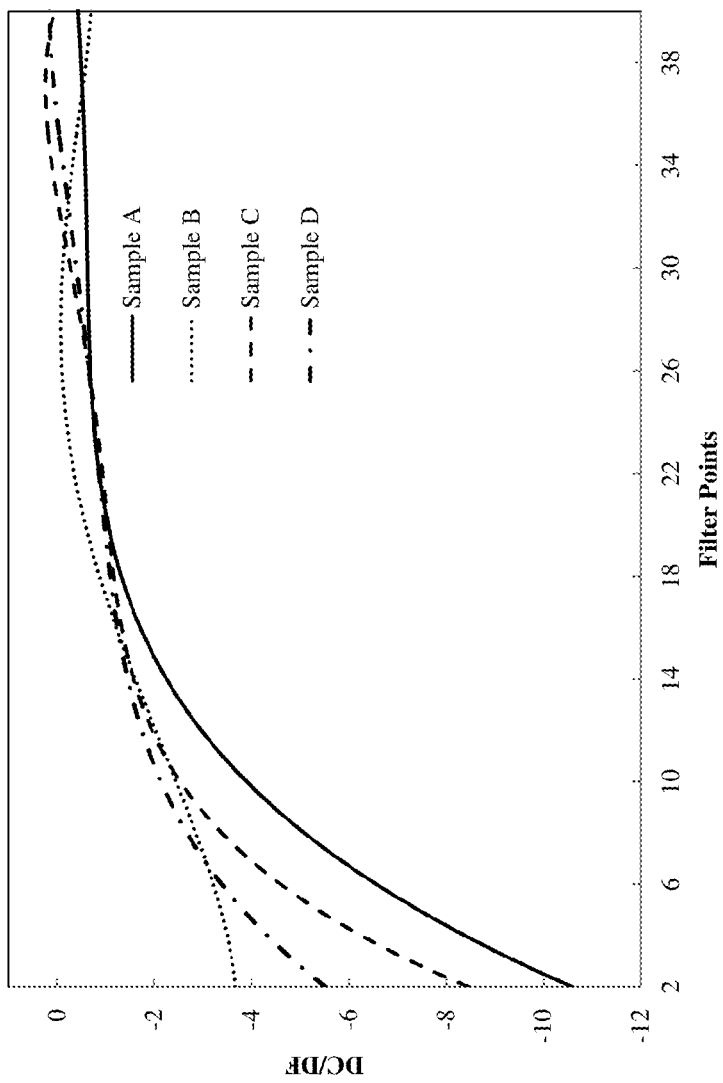
FIG. 11 is a graph of marginal CSI values from tissue sample images in FIG. 9.

Application of the marginal slope analysis for the sample set of images (FIG. 9) is shown in FIG. 11. In this case, DC/DF represents the change in crepe frequency over the change in filter points used in the Savitsky-Golay filtering performed on each row of pixels. As the number of points used in the filter increases, the change in crepe frequency asymptotically approaches a consistent value, i.e., as the filter points go to infinity DC/DF goes to zero because the variations in the line profile are completely smoothed out. Therefore, marginal slope analysis will show the greatest change starting at lower filter points. For imaged samples with high periodicity, e.g., sample B, and/or large crepe structures, the marginal slope shows the least sensitivity because the overall underlying pattern is retained. In contrast, samples with higher randomness and crepe frequency, e.g., sample A, will have higher sensitivity to the change in the number of points used for filtering. A summary of the marginal slope results is presented in Table IV for the initial slope, e.g., points 2-10 in FIG. 11.

TABLE 4

Summary of marginal slope analysis results for the sample set of images in FIG. 9.

| Sample | CBI | Marginal Slope | Periodicity Ranking | Predicted Surface feel (1 = best, 4 = worst) |
|---|---|---|---|---|
| A | 102 | 1.008 | 4 | 1 |
| B | 81 | 0.114 | 1 | 4 |
| C | 85 | 0.967 | 3 | 2 |
| D | 76 | 0.533 | 2 | 3 |

From Table 4, sample C shows nearly the same marginal slope as sample A, yet the CBI results are significantly different. In this case, the contributing factor is from fractured crepe structures and free fiber ends that increase the marginal slope sensitivity. In addition, the cumulative FFT result for sample C shows some periodicity with distinct peaks at 1.85, 2.32, and 3.24 $mm^{-1}$, but at low amplitude. Contribution from these surface structures affects the periodicity resulting in higher dispersion around the three peaks.

Of the four samples from FIG. 9, sample D has the lowest CBI value and second lowest marginal slope. From the cumulative FFT analysis, sample D has a distinct peak at 2.16 $mm^{-1}$ that has higher amplitude and is narrower compared to the peaks from sample C. The lower marginal slope value results from the larger crepe structures and decreases the sensitivity for the number of filter points used. This sample also has more randomness in the crepe frequency compared to sample B resulting in a lower amplitude.

Based on the cumulative FFT, marginal slope analysis, and CBI for the set of images, periodicity and predicted surface softness ranking is listed in Table 4. As discussed, above sample A has clear differences in CBI, marginal slope, and cumulative FFT spectrum compared to the other samples. Whereas differences between samples B, C, and D are vague if only CBI is used as a comparative metric, thus requiring a more detailed analysis using cumulative FFT and marginal slope analysis.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments described herein and incorporated herein. Finally the invention encompasses any and all compositions disclosed or incorporated herein, any and all apparatuses disclosed or incorporated herein, and/or any and all methods of using those compositions and/or apparatuses disclosed or incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method of measuring the geometric characteristics of a crepe structure on a paper sheet, the method comprising the steps of:
    generating data values representing characteristics of positions on a paper sheet by repeatedly emitting at least two emission beams against each of the positions on the paper sheet and reflecting the two beams off of the positions and into a sensor constructed and arranged to absorb and measure the intensity of the reflected emission beams, wherein the positions on the crepe structure on the paper sheet lie along a substantially straight line extending in a substantially cross machine direction,
    correcting the measured intensity of the data values by using an $n^{th}$ order polynomial fit,
    performing a row-by-row smoothing operation of the corrected data values using a filter algorithm,
    identifying positive to negative transitions within the smoothed data values, and
    correlating the identified positive to negative transitions with previously identified values known to correspond to particular geometric dimensions to determine geometric features of the crepe structure, said determined geometric features comprising a beginning and ending of a crepe feature.

2. The method of claim 1 wherein the emission beams are illuminating light and the sensor is a digital camera coupled to a microscope.

3. The method of claim 1 wherein the emission beams are projected at an angle oblique to the machine direction.

4. The method of claim 1 wherein the emission beams are projected at an angle relative to the plane of the paper sheet.

5. The method of claim 1 wherein the filter algorithm is one selected from a list consisting of FFT, Butterworth, Savitsky-Golay, and any combination thereof.

6. The method of claim 1 further comprising the steps of determining a crepe frequency size distribution and converting the crepe frequency size distribution into a length scale.

7. The method of claim 1 further comprising the step of using more than one filtering algorithm and evaluating results of the filtering algorithms to determine the characteristics of free fiber ends of the paper sheet.

8. The method of claim 1 further comprising the step of recognizing periodicity of peaks in the measured intensity data and using the periodicity to determine the softness of the creped paper sheet.

9. The method of claim 1 further comprising the step of recognizing dispersion of peaks in the measured intensity data and using the dispersion to determine the softness of the creped paper sheet.

10. The method of claim 1 further comprising the step of measuring both sides of the paper sheet, the method utilizing a shutter on each side of the paper sheet, the shutters on both sides constructed and arranged to block the impact of an emission beam against a position on one side of the paper sheet when an emission beam is impacting against the other side and also to alternate between which side is having the emission impacts against.

11. The method of claim 1 in which the measured characteristics are input into a system which has online control of at least a process equipment in a papermaking process, the system constructed and arranged to modify the settings of the process equipment if the measured characteristics are outside of a predetermined acceptable range to induce further measured characteristics to conform to the predetermined acceptable range.

12. An apparatus for measuring the geometric characteristics of a crepe structure on a paper sheet, the apparatus comprising:
    at least two emission sources constructed and arranged to emit emission beams against positions on a paper sheet,
    at least one sensor constructed and arranged to absorb and measure the intensity of the reflected emission beams, and
    at least one data processing device constructed and arranged:
    to generate data values representing characteristics of positions on a paper sheet by repeatedly emitting, to correct the measured intensity of the data values by using an $n^{th}$ order polynomial fit,
    to perform a row-by-row smoothing operation of the corrected data values using a filter algorithm,
    to identify positive to negative transitions within the smoothed data values,
    and to correlate the identified positive to negative transitions with previously identified values known to correspond to particular geometric dimensions to determine geometric features of the crepe structure, said determined geometric features comprising a beginning and ending of a crepe feature.

* * * * *

UNITED STATES PATENT AND TRADEMARK OFFICE
CERTIFICATE OF CORRECTION

PATENT NO. : 9,851,199 B2
APPLICATION NO. : 14/623297
DATED : December 26, 2017
INVENTOR(S) : William A. Von Drasek et al.

Page 1 of 1

It is certified that error appears in the above-identified patent and that said Letters Patent is hereby corrected as shown below:

In the Claims

In Column 15, Claim 3, Line 45, delete "the" and insert -- a --, therefor.

In Column 15, Claim 5, Line 49, delete "Savitsky-Golay," and insert -- Savitzky-Golay, --, therefor.

Signed and Sealed this
Twenty-sixth Day of March, 2019

Andrei Iancu
*Director of the United States Patent and Trademark Office*